US00PP23322P2

(12) United States Plant Patent
Pierce

(10) Patent No.: US PP23,322 P2
(45) Date of Patent: Jan. 8, 2013

(54) ***CALIBRACHOA* PLANT NAMED 'CBRZ0003'**

(50) Latin Name: ***Calibrachoa* hybrid**
Varietal Denomination: CBRZ0003

(75) Inventor: Robert O. Pierce, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/317,061

(22) Filed: Oct. 7, 2011

(51) Int. Cl.
*A01H 5/00* (2006.01)

(52) U.S. Cl. ..... Plt./413

(58) Field of Classification Search ..... Plt./413
See application file for complete search history.

*Primary Examiner* — Annette Para
(74) *Attorney, Agent, or Firm* — Joshua L. Price

(57) ABSTRACT

A new *Calibrachoa* plant named 'CBRZ0003' particularly distinguished by the medium sized red-purple and yellow bi-colored flowers, deep green foliage, well-branched, and mounding plant habit, has more center-flowering and good vigor.

1 Drawing Sheet

Latin name of the genus and species of the plant claimed: *Calibrachoa* hybrid.

Varietal denomination: 'CBRZ0003'.

BACKGROUND OF THE NEW PLANT

The present invention comprises a new *Calibrachoa*, botanically known as *Calibrachoa hybrida*, and hereinafter referred to by the variety name 'CBRZ0003'.

'CBRZ0003' is a product of a planned breeding program. The new cultivar has medium sized red-purple and yellow bi-colored flowers; deep green foliage; well-branched and mounding plant habit; has more center-flowering and good vigor.

'CBRZ0003' originated from a hybridization made in June 2007 in a controlled breeding environment in Gilroy, Calif. USA. The female parent was the unpatented, proprietary plant designated '1886-1', with rose and yellow flower color, lighter green foliage and fewer flowers.

The male parent of 'CBRZ0003' was an unpatented, proprietary plant identified as '1856-3' with deep coral flower color, fewer branches, and is later to flower. The resultant seed was sown in January 2008, in Gilroy, Calif., USA.

'CBRZ0003' was selected as one flowering plant within the progeny of the stated cross in April 2008, in a controlled environment in Gilroy, Calif.

The first act of asexual reproduction of 'CBRZ0003' was accomplished when vegetative cuttings were propagated from the initial selection in April 2008 in a controlled environment in Gilroy, Calif.

BRIEF SUMMARY OF INVENTION

Horticultural examination of plants grown from cuttings of the plant initiated in April, 2008, and continuing thereafter, has demonstrated that the combination of characteristics as herein disclosed for 'CBRZ0003' are firmly fixed and are retained through successive generations of asexual reproduction.

'CBRZ0003' has not been observed under all possible environmental conditions. The phenotype may vary significantly with variations in environment such as temperature, light intensity and day length.

A Plant Breeder's Right for this cultivar was applied for in Canada on Dec. 17, 2010, # 10-7124. 'CBRZ0003' has not been made publicly available more than one year prior to the filing of this application.

The following traits have been repeatedly observed and are determined to be basic characteristics of the new variety. The combination of these characteristics distinguishes this *Calibrachoa* as a new and distinct variety.

BRIEF DESCRIPTION OF THE PHOTOGRAPHS

The accompanying photographic drawing shows typical flower and foliage characteristics of 'CBRZ0003' with colors being as true as possible with an illustration of this type. The photographic drawing shows a flowering plant of the new variety, and a close-up of the flowers.

DETAILED BOTANICAL DESCRIPTION

The aforementioned photographs were taken in early April, 2001 from plants growing in a greenhouse trial growing in Gilroy, Calif. These plants were growing in 4.5 inch pots, and were approximately 13 weeks of age. The descriptions and measurements in were taken in later April, 2011, and the plants were then approximately 15-16 weeks of age.

Color references are made to The Royal Horticultural Society Colour Chart (R.H.S.) 2001.

TABLE 1

DIFFERENCES BETWEEN THE NEW VARIETY 'CBRZ0003' AND A SIMILAR VARIETY:

| | 'CBRZ0003' | 'Sunbelkupapi' (U.S. Plant Pat. No. 15,823) |
|---|---|---|
| Flower color: | Yellow morn pattern | White morn pattern |
| Plant habit: | More compact | Less compact |
| Branching: | More basal branching | Fewer basal branching |

Plant:

*Form, growth and habit*.—Initially mounding, then a little more spreading habit, pinching enhances the quantity of branches.

*Plant height*.—5.5-7.4 cm.

*Plant height* (*inflorescence included*).—About 8.5-10.3 cm.

*Plant width*.—About 34.0-43.0 cm.

Roots:

*Number of days to initiate roots and produce a rooted cutting*.—25-28 days at about 22 degrees C.

*Type*.—Fine, fibrous, free branching.

*Color*.—RHS N155B but whiter.

Foliage:

*Arrangement*.—Alternate, simple.

*Immature, leaf color, upper surface*.—Closest to RHS 137A.

*Lower surface*.—RHS 137C but a little greyer.

*Mature, leaf color, upper surface*.—Between RHS 137A and RHS 137B.

*Lower surface*.—RHS 137C but a little greyer.

*Length*.—2.8-3.1 cm.

*Width*.—0.6-0.75 cm.

*Shape*.—Narrowly elliptical.

*Base shape*.—Acuminate.

*Apex shape*.—Obtuse.

*Margin*.—Entire.

*Texture, upper surface*.—Pubescent.

*Lower surface*.—Pubescent.

*Color of veins, upper surface*.—RHS 144A.

*Color of veins, lower surface*.—RHS 144A.

*Petiole color*.—RHS 144B.

*Length*.—0.2-0.3 cm.

*Diameter*.—0.1 cm.

*Texture*.—Pubescent.

Stem:

*Quantity of main branches per plant*.—8-10.

*Color of stem*.—RHS 144B.

*Length of stem*.—About 20.0-25.0 cm.

*Diameter*.—0.15 cm.

*Length of internodes*.—0.9-1.8 cm.

*Texture*.—Hirsute, pubescent.

*Color of pedicel*.—RHS 144B.

*Length of pedicel*.—1.0-1.2 cm.

*Diameter of pedicel*.—0.1 cm.

*Texture of pedicel*.—Hirsute, few glandular hairs.

Inflorescence:

*Type of inflorescence*.—Flowers solitary in upper leaf axis; flowers face mainly horizontally, mostly 5 fused lobes forming a funnel form flower. Continuous flowering throughout the Summer.

*Quantity of inflorescences per plant*.—60-80.

*Lastingness of individual blooms on the plant*.—About 7-9 days.

*Fragrance*.—None.

Bud (just when opening/showing color):

*Color*.—RHS 51C.

*Length*.—2.0.

*Width*.—0.4-0.5 cm.

*Shape*.—Oblong.

Immature inflorescence:

*Flower horizontal diameter*.—2.5 cm.

*Color petals, upper surface*.—RHS 1A at the corolla opening, overlaid with RHS 61B at the margins fading to RHS 61C as it blends with the yellow at the throat; RHS 61A mid-veins and RHS 61B veining.

*Color petals, lower surface*.—RHS 39C with RHS 144B mid-veining and RHS 151A veins.

Mature inflorescence:

*Flower horizontal diameter*.—3.3-3.5 cm.

*Flower height* (*vertical*).—2.8-2.9 cm.

*Color petals, upper surface*.—RHS 2B at the corolla opening, overlaid with RHS 61B to RHS 61C at the margins fading to RHS 61D as it blends with the yellow at the throat; RHS 61B mid-veins and RHS 61C veining.

*Color petals, lower surface*.—RHS 39C with RHS 144B mid-veining and RHS 151A veins.

*Apex shape*.—Rounded.

*Margin*.—Entire.

*Waviness of petals*.—Slight.

*Petal lobation*.—Moderate.

*Petal texture*.—Papillose.

*Corolla tube color outside*.—RHS 8B to RHS 8C with RHS 144B mid-veins.

*Inside*.—RHS 1A to RHS 3B with RHS 144B mid-veining and RHS 151C veining.

*Corolla tube length*.—1.5 cm.

*Corolla texture, outside*.—Hirsute.

*Inside*.—Papillose.

Sepals:

*Color, upper surface*.—Closest to RHS 143B.

*Lower surface*.—Closest to RHS 143A with RHS 137C at the apex.

*Length*.—1.2-1.3 cm.

*Width*.—0.2-0.3 cm.

*Shape*.—Lanceolate.

*Apex shape*.—Acute.

*Based*.—Fused.

*Margins*.—Entire.

*Texture, upper surface*.—Glabrous.

*Lower surface*.—Hirsute.

Reproductive organs:

*Pistil*.—1.

*Length*.—1.0 cm.

*Style color*.—RHS 145B.

*Style length*.—0.6-0.7 cm.

*Stigma color*.—RHS 144B.

*Ovary color*.—RHS 150C.

*Stamens*.—1.

*Color of filaments*.—RHS 150D.

*Length filaments*.—0.4-0.6 cm.

*Anther color*.—RHS 6C.

*Anther length*.—0.1 cm.

*Anther shape*.—Oblong.

*Color of pollen*.—Not observed.

*Pollen amount*.—Not observed.

*Fertility/seed set*.—Has not been observed on this hybrid.

Disease/pest resistance: Disease/pest resistance has not been observed on this hybrid.

What is claimed is:

1. A new and distinct variety of *Calibrachoa* plant named 'CBRZ0003' substantially as illustrated and described herein.

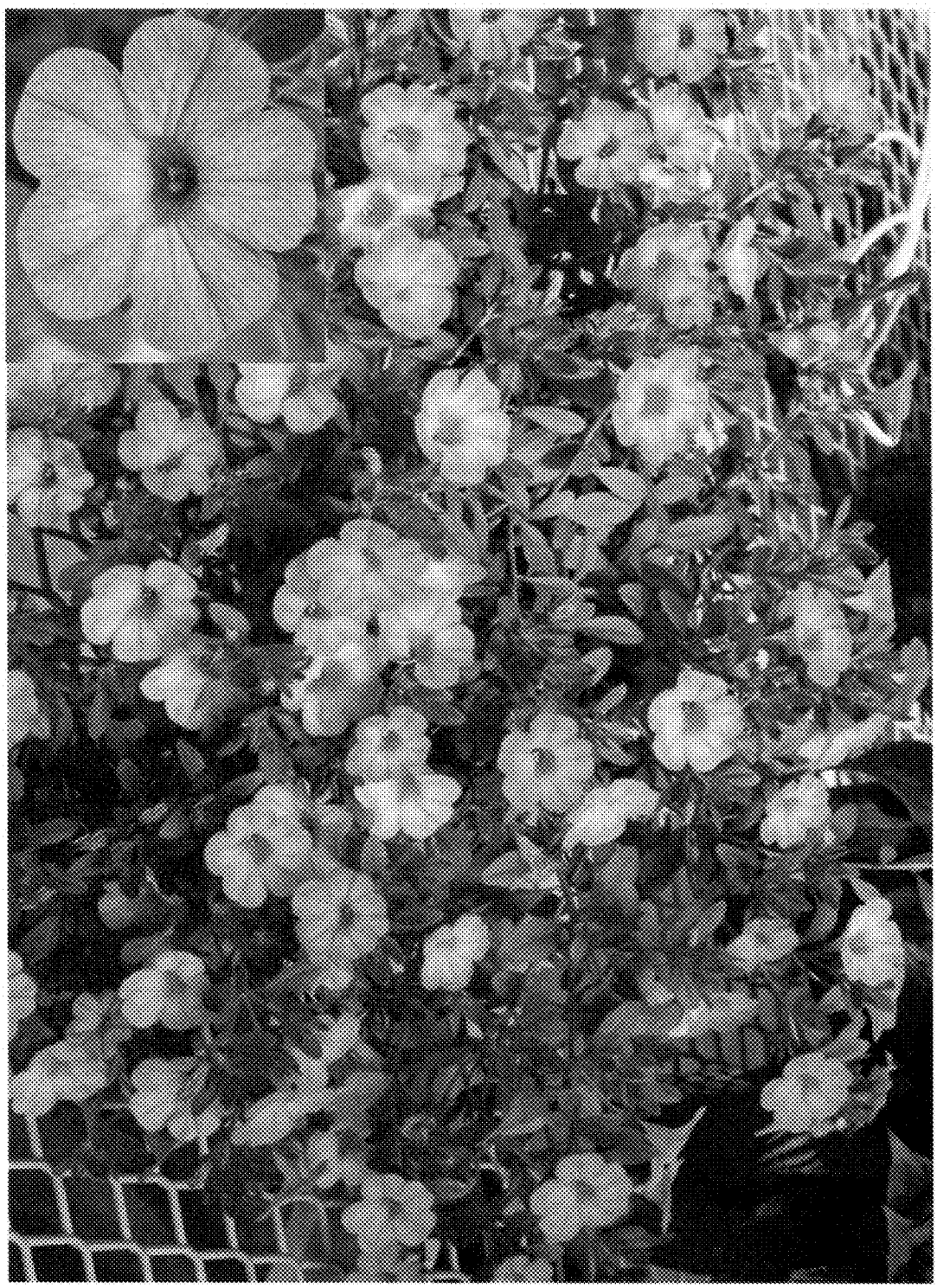

* * * * *